United States Patent
Waldenburg

(10) Patent No.: US 11,231,428 B1
(45) Date of Patent: Jan. 25, 2022

(54) KIT FOR AND METHOD OF TESTING OCCULT BLOOD IN FECES

(71) Applicant: Ottfried Waldenburg, Tucson, AZ (US)

(72) Inventor: Ottfried Waldenburg, Tucson, AZ (US)

( * ) Notice: Subject to any disclaimer, the term of this patent is extended or adjusted under 35 U.S.C. 154(b) by 0 days.

(21) Appl. No.: 15/930,751

(22) Filed: May 13, 2020

(51) Int. Cl.
| | |
|---|---|
| *G01N 33/72* | (2006.01) |
| *G01N 21/78* | (2006.01) |
| *G01N 31/22* | (2006.01) |

(52) U.S. Cl.
CPC .......... *G01N 33/726* (2013.01); *G01N 21/78* (2013.01); *G01N 31/22* (2013.01); *G01N 33/725* (2013.01)

(58) Field of Classification Search
CPC .... G01N 33/72; G01N 33/721; G01N 33/725; G01N 33/726; G01N 21/77; G01N 21/78; G01N 31/22; Y10T 436/206664
USPC .... 436/63, 66, 135, 164, 165, 169; 422/400, 422/408, 409, 413, 418, 420, 430, 555
See application file for complete search history.

(56) References Cited

U.S. PATENT DOCUMENTS

| | | | | | |
|---|---|---|---|---|---|
| 4,511,533 | A | * | 4/1985 | Guadagno | G01N 33/726 206/205 |
| 4,521,520 | A | * | 6/1985 | Jacke | G01N 33/726 4/144.2 |
| 4,541,987 | A | * | 9/1985 | Guadagno | G01N 33/725 422/401 |
| 4,804,518 | A | * | 2/1989 | Levine | G01N 33/528 422/401 |
| 4,956,300 | A | * | 9/1990 | Wells | G01N 33/725 264/122 |
| 5,840,584 | A | * | 11/1998 | Waldenburg | G01N 33/72 436/66 |
| 6,077,711 | A | * | 6/2000 | Singer | B01L 3/502 422/411 |
| 6,436,714 | B1 | * | 8/2002 | Clawson | B01L 3/5055 422/411 |
| 7,288,413 | B2 | * | 10/2007 | Goulden | G01N 33/558 422/535 |
| 7,517,691 | B2 | * | 4/2009 | Waldenburg | A61B 10/0038 422/409 |
| 2010/0111763 | A1 | * | 5/2010 | Kahn | G01N 33/586 422/400 |

* cited by examiner

*Primary Examiner* — Maureen Wallenhorst
(74) *Attorney, Agent, or Firm* — John J. Connors; Connors & Assoc.

(57) ABSTRACT

A kit and method are used to detect the presence of occult blood in feces. The kit has a closed and sealed package containing a sheet of absorbent material impregnated with a guaiac material and a friable packet holding a hydrogen peroxide solution. The packet is sealed to prevent the solution from escaping the packet until it is manually fracture. With the sheet and the packet both within the closed package and in contact with each other, a user manually compresses the packet to break the packet and release the solution, which is absorbed by the sheet material. The package remains closed for a sufficient time for the solution to be absorbed by the sheet. The user then opens the packaging and removes the sheet that is now wetted with the solution, using the sheet in the conventional manner to collect a feces sample. A blue color appearing on the sheet indicates the presence of occult blood in the feces sample.

1 Claim, 4 Drawing Sheets

Text

KIT FOR AND METHOD OF TESTING OCCULT BLOOD IN FECES

INCORPORATION BY REFERENCE

Any and all U. S. patents, U. S. patent applications, and other documents, hard copy or electronic, cited or referred to in this application are incorporated herein by reference and made a part of this application.

Definitions

The words "comprising," "having," "containing," "holding," and "including," and other grammatical forms thereof, are intended to be equivalent in meaning and be open ended in that an item or items following any one of these words is not meant to be an exhaustive listing of such item or items, nor meant to be limited to only the listed item or items.

BACKGROUND OF INVENTION

Occult blood in feces is an early sign of intestinal cancer or other disorders. It is undetectable to the naked eye, because the blood is present in minuet amounts. A well-known test method employs guaiac resin material. This material reacts with a peroxide in the presents of occult blood in feces to produce a blue color. A variety of guaiac materials maybe employed as well as various peroxide materials. Various test devices have been suggested, for example in U.S. Pat. Nos. 4,511,533; 4,541,987; and 5,840,584.

SUMMARY

My kit and method are an improvement in the well-known test methods employing guaiac resin material and have one or more of the features depicted in the embodiment discussed in the section entitled "DETAILED DESCRIPTION OF ONE ILLUSTRATIVE EMBODIMENT." These features are not listed in any rank order nor is this list intended to be exhaustive. The claims that follow define my kit and method, distinguishing them from the prior art; however, without limiting the scope of my kit and method as expressed by these claims, in general terms, some, but not necessarily all, of their features are:

My method of detecting the presence of occult blood in feces employs a kit comprising a closed and sealed waterproof package containing a sheet of an activated absorbent material impregnated with a guaiac material and a sealed friable packet holding a standard developing solution. The absorbent material and the packet are both within the closed package and adjacent each other. Upon a user manually compressing the sealed friable packet while this packet is within the closed and sealed waterproof package breaks the packet, releasing the solution. The package remains closed for a sufficient time for the solution to be absorbed by the sheet. After the elapse of this time, the user opens the packaging and removes the impregnated sheet of absorbent material, and then collects a sample of the feces being tested on the impregnated sheet of absorbent material. The appearance of a blue color on the impregnated sheet of absorbent material indicates the presence of occult blood. The standard developing solution includes hydrogen peroxide and the balance water. The kit may include a HEMI test solution dispenser for confirming that the sheet is still reactive.

DRAWING

One embodiment of my kit and method are discussed in detail in connection with the accompanying drawing, which is for illustrative purposes only. This drawing includes the following figures (Figs.), with like numerals and letters indicating like parts:

DETAILED DESCRIPTION OF ONE ILLUSTRATIVE EMBODIMENT

Kit

Figure 5:
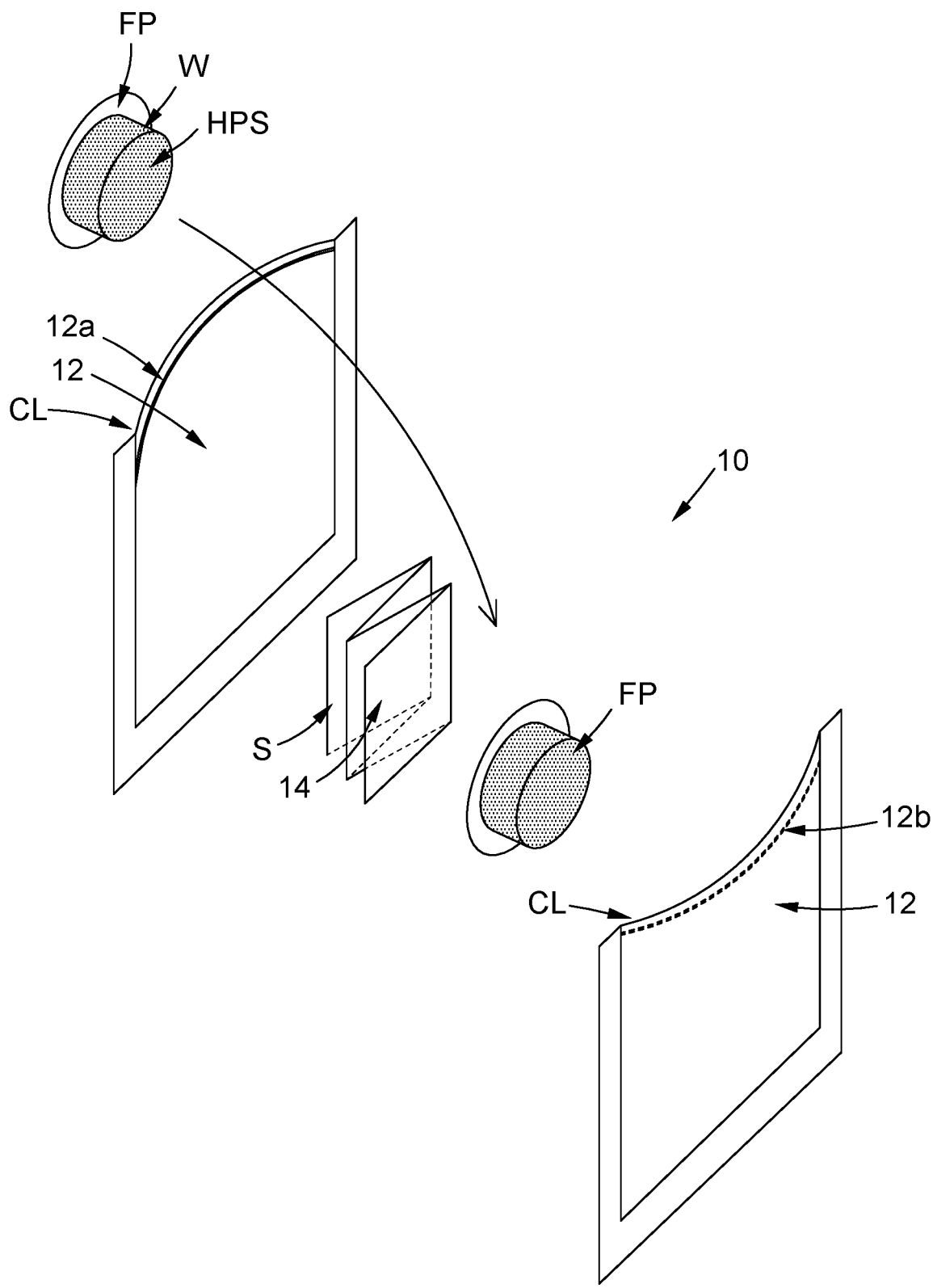
FIG. 5 is an exploded perspective view of the package shown in FIG. 1.
Figure 6:
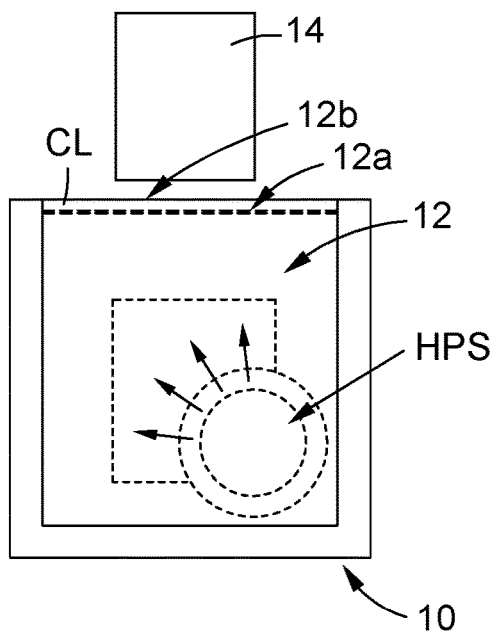
FIG. 6 is plan view illustrating removing the sheet component soaked with hydrogen peroxide solution after first compressing the packet component of the kit while the sheet component of the kit is within the closed and seal package.

As best depicted in FIGS. 6 through 12, my kit, generally designated by the numeral 10, is used to detect the presence of occult blood in feces. As shown in FIG. 5, it comprises a water proof, opaque package 12 holding a sheet 14 of absorbent material and a friable packet FP. The friable packet FP contains a standard developer solution SDS, typically comprising hydrogen peroxide and denatured ethyl alcohol, for example). The package 12 may be a conventional plastic bag with a zipper-type closure CL along one edge ED1. A suitable plastic bag is sold under the trademark Ziploc.

Figure 3:
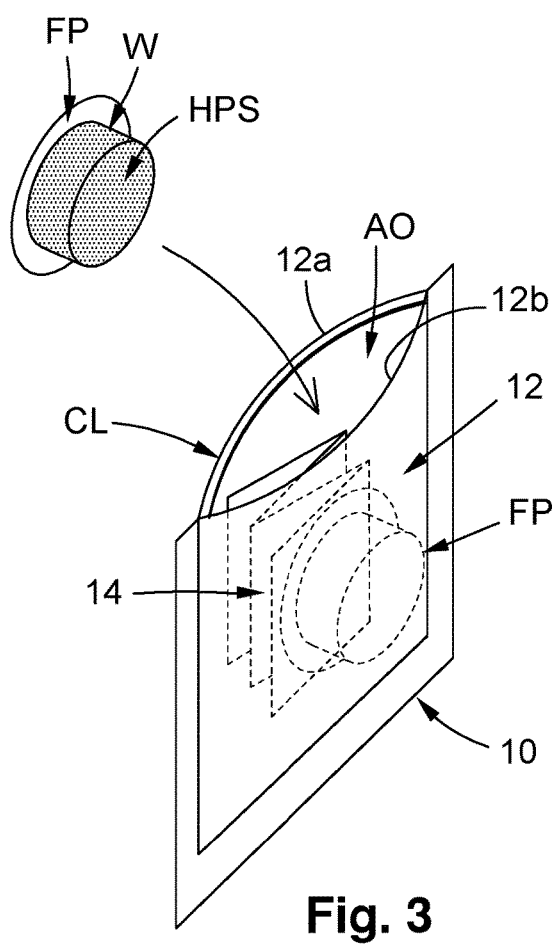
FIG. 3 is a perspective view of the components of the kit being assembled into the package shown in FIG. 1.

The sealed closure CL has aligned, interlocking elements 12a and 12b at the edge ED1 that normally are engaged to close an access opening AO to the interior of the package 12 and provide an air and water tight seal. Upon manually pulling the interlocking elements 12a and 12b apart, the access opening AO is uncovered to allow removal of the kit components when the kit is to be used. And, as shown in FIG. 3, the access opening AO when uncovered during manufacture of the kit 10, allows the kit components to be placed into the plastic bag's interior in the positions shown in FIG. 4.

Figure 1:
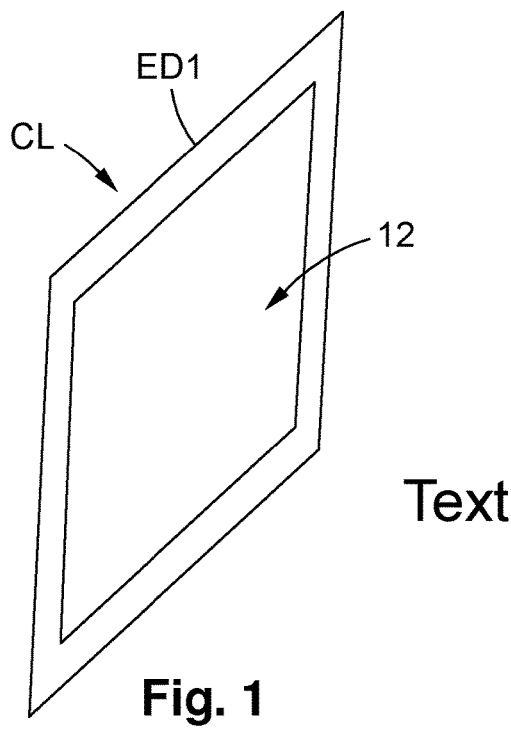
FIG. 1 is a perspective view of a closed and sealed package containing my kit shown in FIG. 5.
Figure 2:
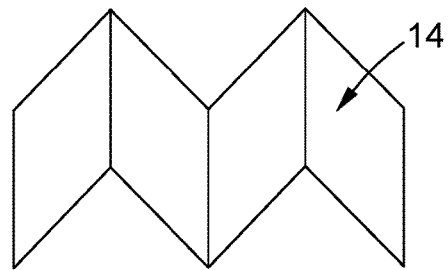
FIG. 2 is a perspective view of an unfolded absorbent sheet component of my kit shown in FIG. 5.
Figure 4:
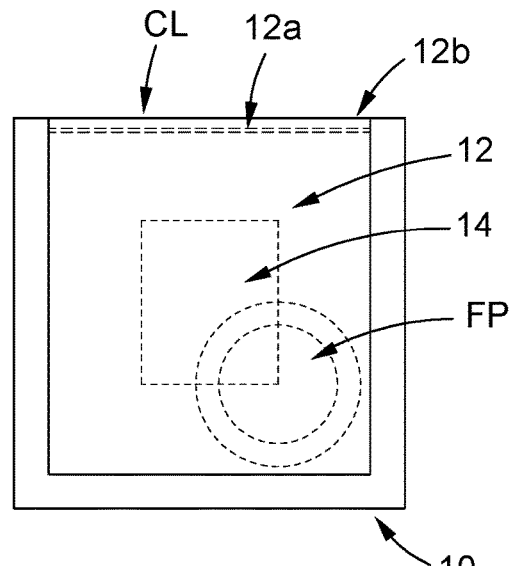
FIG. 4 is a plan view of the package shown in FIG. 1 with kit components shown in dotted lines depicting a nominal position of these components within the package after being assembled as shown in FIG. 3.

The sheet 14 may be an absorbent paper impregnated with a guaiac material. A suitable sheet 14 is available from GE Healthcare Life Sciences under the Cenogenics label. As illustrated in FIG. 2, the sheet 14 may be folded into a stack 14a (FIG. 3) of overlying sections S. As depicted in FIG. 3, the friable packet FP may be inserted adjacent the stack 14a. Alternately, the friable packet FP may be inserted centrally between the sheet's sections S, or at a corner of a stack as depicted in FIG. 4. With the friable packet FP so positioned with respect to the sheet 14, the plastic package 12 is closed and sealed by zipping up the zipper-type closure CL.

Method

With the kit 10 so assembled, it is ready for use. The user first manually compresses the friable packet FP while within the package 12, breaking a wall W of the packet to release the hydrogen peroxide solution HPS. This hydrogen peroxide solution HPS is retained in the closed plastic bag 12 for a sufficient time for the solution to be absorbed by the sheet 14, impregnating the sheet.

Figure 7:
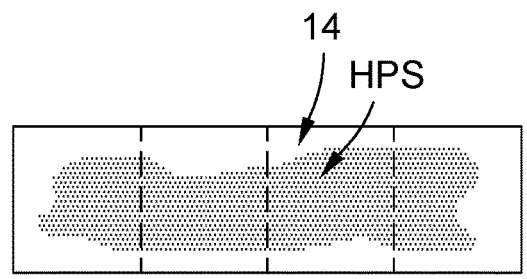
FIG. 7 is a plan view of the unfolded the sheet component removed from the package and impregnated with the hydrogen peroxide solution released upon compressing the packet component while within the sealed package.
Figure 8:
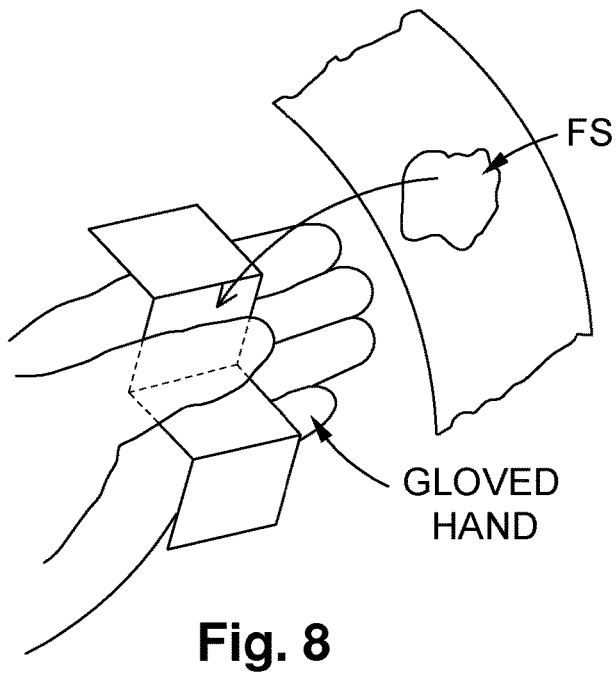
FIG. 8 is a plan view illustrating collecting a sample of feces on the impregnated sheet of absorbent sheet component by removal from toilet tissue used to collect a sample of a patient's feces.
Figure 9:
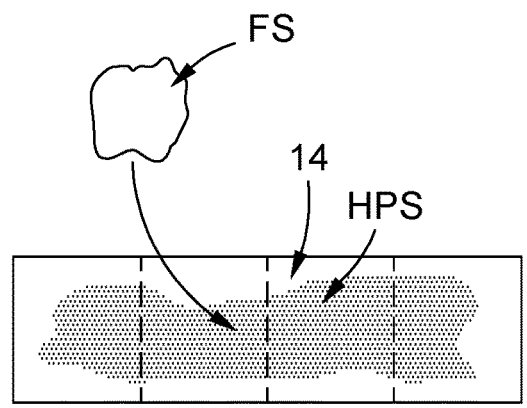
FIG. 9 is a plan view of the absorbent sheet material shown in FIG. 7 using the impregnated sheet of absorbent sheet to collect a sample of a patient's feces directly.
Figure 10:
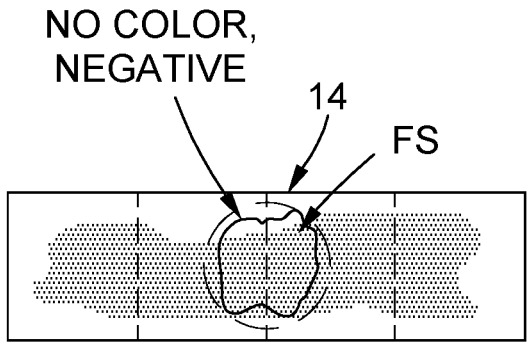
FIG. 10 is a plan view of the absorbent sheet material depicting the failure of a blue color appearing on the sheet material upon contact with the sample of feces, indicating a negative test, that is, the absence of blood in the sample.
Figure 11:
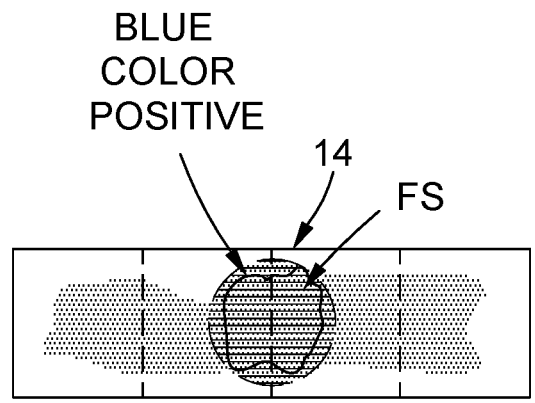
FIG. 11 is a plan view of the absorbent sheet material depicting a blue color appearing on the sheet material upon contact with the sample of feces, indicating a positive test, that is, presence of blood in the sample.

Typically, within at least 2 minutes after breaking the friable packet FP, the user opens the package 12 and, as depicted in FIG. 7, removes the sheet 14 impregnated with the hydrogen peroxide solution HPS and collects a sample of feces FS. This collection may be indirectly using toilet tissue as illustrated in FIG. 8, avoiding skin contact with the feces. Or, the sheet 14 may be used directly as toilet paper as shown in FIG. 9. As illustrated in FIG. 10, a blue color spot appearing on the surface of sheet 14 where contact with the patient's feces occurred is a positive indicator of the presence of occult blood in the feces sample. The absence of such blue color where contact was made with the sample of the patient's feces as shown in FIG. 10 is a negative indicator of the presence of occult blood in the feces sample.

Figure 12:
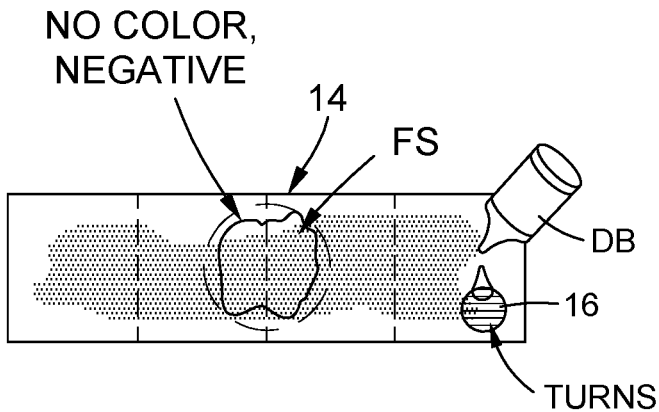
FIG. 12 is a plan view of the absorbent sheet material of FIG. 10 being tested with a drop of HEMI solution to confirm that the sheet material is active and will respond in the presence of blood.

A FDA confirmation test is provided to be sure that the guaiac material in the sheet 14 is reactive. A common test for such reactivity is the reaction of a standard HEMI test solution with the guaiac material in the sheet 14 to produce the blue color appearing in the presence of blood. As depicted in FIG. 12, a plastic dropper bottle DB containing this test solution is manually squeezed to release a drop of the test solution on the sheet 14 depicted in FIG. 10. If a blue spot 16 appears where the drop contact the sheet, the color blue appears, confirming that the sheet 14 is still reactive. If not, the test is a failure because the sheet is not reactive and the test must be repeated with an active sheet 14.

A customer purchasing the kit 10 may at the same time buy the dropper bottle DB as a separate item or the bottle may be included with the purchase of the kit.

SCOPE OF THE INVENTION

The above presents a description of the best mode I contemplate of carrying out my kit and method, and of the manner and process of making and using them, in such full, clear, concise, and exact terms as to enable a person skilled in the art to make and use. My kit and method is, however, susceptible to modifications and alternate constructions from the illustrative embodiment discussed above which are fully equivalent. Consequently, it is not the intention to limit my kit and method to the particular embodiment disclosed. On the contrary, my intention is to cover all modifications and alternate constructions coming within the spirit and scope of my kit and method as generally expressed by the following claims, which particularly point out and distinctly claim the subject matter of my invention:

The invention claimed is:

1. A kit for detecting occult blood in feces, comprising
   (i) a package configured to be opened and closed that, when opened, allows an absorbent sheet and a sealed friable packet to be placed within the package through an opening, and that when closed, provides a waterproof seal of the package with said absorbent sheet and said sealed friable packet located inside the package,
   said absorbent sheet impregnated with a guaiac material and said sealed friable packet enclosing a hydrogen peroxide aqueous solution that upon compression releases from the packet the solution that remains in the package when the opening is closed while the packet is within the sealed package,
   said package closed to prevent the escape of liquid from the package and said packet positioned in the package with respect to the absorbent sheet so that manually compressing the packet while within the package breaks the packet to release the solution which is retained in the closed package and impregnates the absorbent sheet, and
   (ii) a separate dispenser of a test solution that on release and contact with the absorbent sheet produces a color change on the absorbent sheet that confirms that the absorbent sheet is still reactive,
   said dispenser comprising a dropper bottle containing the test solution and adapted to be manually squeezed to release a drop of the test solution on the absorbent sheet.

* * * * *